United States Patent [19]

Bartels et al.

[11] Patent Number: 4,941,976
[45] Date of Patent: * Jul. 17, 1990

[54] DEHYDRATION OF GLYCOLS

[75] Inventors: Craig R. Bartels; John Reale, Jr., both of Wappingers Falls, N.Y.

[73] Assignee: Texaco Inc., White Plains, N.Y.

[*] Notice: The portion of the term of this patent subsequent to Feb. 7, 2006 has been disclaimed.

[21] Appl. No.: 235,082

[22] Filed: Aug. 23, 1988

Related U.S. Application Data

[63] Continuation of Ser. No. 97,766, Sep. 17, 1987, Pat. No. 4,802,988.

[51] Int. Cl.$^5$ .............................................. B01D 69/00
[52] U.S. Cl. ................................ 210/490; 210/500.41; 210/500.42; 428/220; 428/319.9; 428/419; 428/524
[58] Field of Search ...................... 210/500.41, 500.42, 210/490; 428/220, 319.9, 419, 524

[56] References Cited

U.S. PATENT DOCUMENTS

| 3,556,305 | 1/1971 | Shorr | 210/500.41 |
|---|---|---|---|
| 4,046,843 | 9/1977 | Sano et al. | 210/500.42 |
| 4,385,094 | 5/1983 | Tanaka et al. | 210/500.42 |
| 4,619,767 | 10/1986 | Kamiyama et al. | 210/500.42 |
| 4,737,325 | 4/1988 | Kamiyama et al. | 210/500.42 |
| 4,755,299 | 7/1988 | Brüschke | 210/500.42 |
| 4,802,988 | 2/1989 | Bartels et al. | 210/640 |
| 4,834,886 | 5/1989 | Cadotte | 210/490 |

FOREIGN PATENT DOCUMENTS

| 1093806 | 5/1986 | Japan | 210/500.42 |
|---|---|---|---|
| 1268302 | 11/1986 | Japan | 210/500.41 |
| 2171712 | 7/1987 | Japan | 210/500.42 |

OTHER PUBLICATIONS

"Studies on Syntheses and Permeability of Special Polymer Membranes", Uragami, Tadashi, Wada, Tamaki, Sugihara, Mizuko, Angew. Makromol. Chem. 138, 173-83 (1986).

Primary Examiner—W. Gary Jones
Attorney, Agent, or Firm—Robert A. Kulason; James J. O'Loughlin; Carl G. Seutter

[57] ABSTRACT

Concentration of aqueous solutions of ethylene glycol may be effected by a composite membrane including a glutaraldehyde-crosslinked polyvinyl alcohol bonded to a porous layer of polysulfone on a polyester backing.

5 Claims, No Drawings

DEHYDRATION OF GLYCOLS

This is a continuation of application Ser. No. 097,766, filed Sept. 17, 1987, now U.S. Pat. No. 4,802,988.

FIELD OF THE INVENTION

This invention relates to the dehydration of glycols such as ethylene glycol. More particularly it relates to a membrane for effecting separation of water from an aqueous mixture containing a glycol.

BACKGROUND OF THE INVENTION

As is well known to those skilled in the art, it is possible to remove water from mixtures thereof with organic liquids by various techniques including adsorption or distillation. These conventional processes, particularly distillation, are however characterized by high capital cost. In the case of distillation for example the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling—plus pumping, etc.

Furthermore the properties of the materials being separated, as is evidenced by the distillation curves, may be such that a large number of plates may be required, etc. When the material forms an azeotrope with water, additional problems may be present which for example, could require that separation be effected in a series of steps (e.g. as in two towers) or by addition of extraneous materials to the system.

There are also comparable problems which are unique to adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane The permeate is then removed as a vapor from the downstream side of the film—typically by sweeping with a carrier gas or by reducing the pressure below the vapor pressure of the permeating species.

Illustrative membranes which have been employed in prior art techniques include those set forth in the following table:

TABLE

| Separating Layer | References |
| --- | --- |
| Nafion brand of perfluorosulfonic acid | Cabasso and Liu J. Memb. Sci. 24, 101 (1985) |
| Sulfonated polyethylene | Cabasso, Korngold & Liu J. Pol. Sc: Letters, 23, 57 (1985) |
| Fluorinated Polyether or Carboxylic Acid fluorides | USP 4,526,948 to Dupont as assignee of Resnickto |
| Selemion AMV blend of Asahi Glass cross-linked styrene butadiene (with quaternary ammonium residues on a polyvinyl chloride backing | Wentzlaff Boddeker, & Hattanbach J. Memb. Sci. 22, 333 (1985) |
| Cellulose triacetate | Wentzlaff, Boddeker & Hattanback J. Memb Sci 22 333 (1985) |
| Polyacrylontrile | Neel, Aptel, & Clement Desalination 53, 297 (1985) |
| Crosslinked Polyvinyl Alcohol | Eur. Patent 0 096 339 to GFT as assignee, of Bruschke |
| Poly(maleimide-acrylonitrile) | Yoshikawa et al J. Pol. Sci. 22, 2159 (1984) |
| Dextrine isophoronediisocyate | Chem. Econ Eng. Rev., 17, 34, (1985) |

The cost effectiveness of a membrane is determined by the selectivity and productivity. Of the membranes commercially available, an illustrative membrane of high performance is that disclosed in European patent No. 0 096 339 A2 of GFT as assignee of Bruschke—published Dec. 21, 1983.

European Patent No. 0 096 3339 A2 to GFT as assignee of Bruschke discloses, as cross-linking agents, diacids (typified by maleic acid or fumaric acid); dihalogen compounds (typified by dichloroacetone or 1,3-dichloroisopropanol); aldehydes, including dialdehydes, typified by formaldehyde. These membranes are said to be particularly effective for dehydration of aqueous solutions of ethanol or isopropanol.

This reference discloses separation of water from alcohols, ethers, ketones, aldehydes, or acids by use of composite membranes. Specifically the composite includes (i) a backing typically about 120 microns in thickness, on which is positioned (ii) a microporous support layer of a polysulfone or a polyacrylonitrile of about 50 microns thickness, on which is positioned (iii) a separating layer of crosslinked polyvinyl alcohol about 2 microns in thickness.

Polyvinyl alcohol may be cross-linked by use of difunctional agents which react with the hydroxyl group of the polyvinyl alcohol. Typical cross-linking agent may include dialdehydes (which yield acetal linkages), diacids or diacid halides (which yield ester linkages), dihalogen compounds or epichlorhydrin (which yield either linkages) olefinic aldehydes (which yield ether/acetal linkages), boric acid (which yields boric ester linkages), sulfonamidoaldehydes, etc.

See also J. G. Prichard *Polyvinyl Alcohol, Basic Properties and Uses* Gordon and Breach Science Publishers, New York (1970) or C. A. Finch *Polyvinyl Alcohol, Properties and Applications* John Wiley and Sons, New York (1973).

It is an object of this invention to provide a novel composite membrane characterized by its ability to effect separation of water from glycols such as ethylene glycol. Other objects will be apparent to those skilled in the art.

STATEMENT OF THE INVENTION

In accordance with certain of its aspects, this invention is directed to a method of concentrating a charge aqueous solution of a glycol which comprises maintaining a non-porous separating layer of cast polyvinyl alcohol which has been cross-linked with an aliphatic polyaldehyde containing at least three carbon atoms including those in said aldehyde groups;

maintaining a pressure drop across said non-porous separating layer of polyvinyl alcohol;

passing a charge aqueous solution of a glycol into contact with the high pressure side of said non-porous separating layer of polyvinyl alcohol whereby at least a portion of said water in said charge aqueous solution and a lesser portion of glycol in said charge aqueous solution pass by pervaporation through said non-porous separating layer of polyvinyl alcohol as a lean mixture containing more water and less glycol than are present in said charge aqueous solution and said charge aqueous solution is converted to a rich liquid containing less water and more glycol than are present in said charge aqueous solution;

recovering from the low pressure side of said non-porous separating layer of polyvinyl alcohol said lean mixture containing more water and less glycol than are present in said charge aqueous solution, said lean mixture being recovered in vapor phase at a pressure below the vapor pressure thereof; and recovering from the high pressure side of said non-porous separating layer said rich liquid containing a lower water content and a higher glycol content than are present in said charge aqueous solution.

In accordance with certain of its other aspects, this invention is directed to a non-porous separating layer of thickness of 1-10 microns of cast polyvinyl alcohol of molecular weight $\overline{M}_n$ of 20,000-200,000 which has been cross-linked, in the presence of acid catalyst, with an aliphatic polyaldehyde containing at least three carbon atoms including those in said aldehyde groups and thereafter cured at 100° C.-225° C.

DESCRIPTION OF THE INVENTION

The composite structure of this invention includes a multi-layer assembly which in the preferred embodiment preferably includes a porous carrier layer which provides mechanical strength and support to the assembly.

THE CARRIER LAYER

This carrier layer, when used, is characterized by its high degree of porosity and mechanical strength It may be fibrous or non-fibrous, woven or non-woven. In the preferred embodiment, the carrier layer may be a porous, flexible, non-woven fibrous polyester.

A preferred non-woven polyester carrier layer may be formulated of non-woven, thermally-bonded strands and characterized by a fabric weight of 80±8 grams per square yard, a thickness of 4.2±0.5 mils, a tensile strength (in the machine direction) of 31 psi and (in cross direction) of 10 psi, and a Frazier air permeability of 6 cuft/min/sq. ft. @0.5 inches of water.

THE POROUS SUPPORT LAYER

The porous support layer of this invention is preferably formed of a sheet of polysulfone polymer. Typically the polysulfone may be of thickness of 40-80 microns, say 50 microns and of molecular weight $\overline{M}_n$ of 5,000-100,000, preferably 20,000-60,000 say 40,000. The polysulfone is preferably characterized by a pore size of less than about 500 Å and typically about 200 Å. This corresponds to a molecular weight cut-off of less than about 25,000 typically about 20,000.

The sulfone polymers which may be employed may include those made from cumene containing isopropylidene groups in the backbone; e.g.

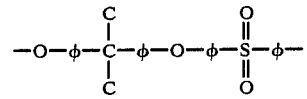

These isopropylidene sulfones containing repeating units including ether-aromatic-isopropylidene-aromatic-ether-aromaticsulfone-aromatic groups may typically have a molecular weight $\overline{M}_n$ of 15,000-30,000, a water absorption (at 20° C.) of about 0.85 w %, a glass transition temperature of 449° K., a density of 1.25 mg/m$^3$, a tensile strength (at 20° C.) at yield of 10,000 psi, and a coefficient of linear thermal expansion of $2.6 \times 10^{-5}$ mm/mm/°C.

It is found, however, that the preferred sulfone polymers which may be employed in practice of the process of this invention, may include those which are free of isopropylidene moieties in the backbone chain and wherein the phenylene group in the backbone are bonded only to ether oxygen atoms and to sulfur atoms. These preferred polymers, which may be typically, be prepared from

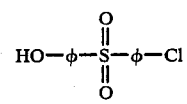

may be characterized by a backbone containing the following repeating groups:

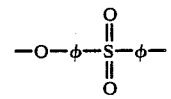

A preferred sulfone polymer may be a polyether sulfone which is free of isopropylidene moieties in the backbone chain and wherein the phenylene groups in the backbone are bonded only to ether-oxygen atoms and to sulfur atoms. This polymer may be characterized by molecular weight $\overline{M}_n$ of 25,000, water absorption @20° C. of 2.1 w %, glass transition temperature of 487° K., tensile strength at yield of 12,200 psig at 20° C.; and coefficient of linear thermal expansion of $5.5 \times 10^{-5}$ mm/mm/°C. This polymer has a molecular weight cut off of about 20,000 and has a pore size of about 200 Å.

THE SEPARATING LAYER

The separating layer which permits attainment of the separation in accordance with this invention includes a non-porous film of cross-linked polyvinyl alcohol of thickness of about 1-10 microns preferably 1-5 microns, say 1.5 microns. The layer is formed from polyvinyl alcohol which has been prepared by hydrolysis of polyvinyl acetate-typically 50-100% hydrolyzed, preferably 90-100%, say 100% hydrolyzed. The charge polyvinyl alcohol has a molecular weight of 20,000-200,000 say 115,000. Typically it may be employed as a 5-10 w %, say 7 w % aqueous solution A commercially available product which may be employed is the Aldrich brand of 100% hydrolyzed polyvinyl alcohol of molecular weight of about 115,000 as a 7 w % aqueous solution.

It is a feature of this invention that the membrane or sheet of cross-linked polyvinyl alcohol separating layer is formed in situ on the porous support layer This is effected by use, as a cross linking agent, of an aliphatic dialdehyde containing at least three carbon atoms. Preferably the aliphatic dialdehyde may contain 3-8 carbon atoms, most preferably 5 carbon atoms. Typical alphatic dialdehydes which may be employed may include:

TABLE

| |
| --- |
| glutaraldehyde |
| 2-hydroxyhexanedial - 1,6 |
| malonic dialdehyde |
| succinic dialdehyde |
| heptanedial - 1,6 |

The preferred alphatic dialdehyde is glutaraldehyde. Aldehydes falling outside the scope of this invention typified by formaldehyde, glyoxal, or succinic semi aldehyde yield membranes which are characterized by unsatisfactory performance. Performance is judged by the ability of a membrane system to give a permeate containing less than 1 w % ethylene glycol (from a charge containing 85 w % ethylene glycol and 15 w % water) with a flux of at least 0.5 kilograms/meter$^2$hour (kmh) at a feed temperature of 80° C. and with a permeate pressure of 5 mmHg and a condenser cooled by liquid nitrogen). Compositions falling outside the scope of this invention may be characterized by unsatisfactory selectivity or unsatisfactory productivity or both.

In situ crosslinking may be carried out by casting 5-10 w %, say 7 w % aqueous solution of polyvinyl alcohol which contains the aliphatic dialdehyde cross-linking agent. The mole ratio of crosslinking agent to polyvinyl alcohol may be 0.05-0.30, say 0.2.

Crosslinking is carried out, in the presence of acid catalyst, preferably inorganic acid. Sulfuric acid is preferred. Hydrochloric acid is much less preferred—because it yields membranes of poor selectivity, although the flux may be high.

It may be possible in one embodiment to crosslink the polyvinyl alcohol separating layer in one step by adding to the aqueous solution of polyvinyl alcohol and dialdehyde, the acid catalyst, preferably sulfuric acid, in mole ratio of acid to dialdehyde of 0.08-0.14, say 0.1.

In another embodiment, it may be possible to apply to the porous support layer, an aqueous solution of polyvinyl alcohol and dialdehyde. This may be dried at 40° C.-80° C., say 50° C. for 2-10 minutes, say 4 minutes to form a film. There may then be added onto the surface of this film a viscous solution containing 2-7 w %, say 3.5 w % of polyvinyl alcohol and having a mole ratio of sulfuric acid to dialdehyde of 0.08-0.14, preferably 0.1.

The composite membrate, whether prepared by the one-step or the two-step process may then be cured in an oven at 100° C.-200° C., say 125° C. for 1-30 minutes, say 2 minutes to yield a polyvinyl alcohol film having a thickness of 1-10 microns, say 3 microns.

THE COMPOSITE MEMBRANE

It is a feature of this invention that the composite membrane of this invention may comprise (i) an optional carrier layer, characterized by porosity and mechanical strength, for supporting a porous support layer and a separating layer, (ii) a polysulfone porous support layer of molecular weight of 5,000-100,000, of thickness of 10-80 microns, and of molecular weight $\overline{M}_n$ cut off of 25,000-100,000 and (iii) as a non-porous separating layer polyvinyl alcohol of molecular weight of 20,000-200,000 which has been crosslinked with an aliphatic dialdehyde containing 3-8 carbon atoms.

The composite membranes of this invention may be utilized in various configurations. It is, for example, possible to utilize the composite in a plate and-frame configuration in which separating layers may be mounted on the porous support layer with the carrier layer.

It is possible to utilize a spiral mound module which includes a non-porous separating layer membrane mounted on a porous support layer and a carrier layer, the assembly being typically folded and bonded or sealed along all the edges but an open edge—to form a bag-like unit which preferably has the separating layer on the outside. A cloth spacer, serving as the permeate or discharge channel is placed within the bag-like unit. The discharge channel projects from the open end of the unit.

There then placed on one face of the bag-like unit, adjacent to the separating layer, and coterminous therewith, a feed channel sheet—typically formed of a plastic net.

The so-formed assembly is wrapped around a preferably cylindrical conduit which bears a plurality of perforations in the wall—preferably in a linear array which is as long as the width of the bag-like unit. The projecting portion of the discharge channel of the bag-like unit is placed over the performations of the conduit; and the bag-like unit is wrapped around the conduit to from a spiral wound configuration It will be apparent that, although only one feed channel is present, the single feed channel in the wound assembly will be adjacent to two faces of the membrane layer. The spiral wound configuration may be formed by wrapping the assembly around the conduit a plurality of times to form a readily handlable unit. The unit is fitted within a shell (in manner comparable to a shell-and-tube heat exchanger) provided with an inlet at one end and an outlet at the other A bafflu-like seal between the inner surface of the shell and the outer surface of the spiral-wound input prevents fluid from bypassing the operative membrane system and insures that fluid enters the system principally at one end. The permeate passes from the feed channel, into contact with the separating layer and thence therethrough, into the permeate channel and thence therealong to and through the perforations in the conduit through which it is withdrawn as net permeate.

In use of the spiral wound membrane, charge liquid is permitted to pass through the plastic net which serves as a feed channel and thence into contact with the non-porous separating membranes. The liquid which does not pass through the membranes is withdrawn as retentate. The liquid or vapor which permeates the membrane passes into the volume occupied by the permeate spacer and through this permeate channel to the perforations in the cylindrical conduit through which it is withdrawn from the system. In this embodiment, it will be apparent that they system may not include a carrier layer.

In another embodiment, it is possible to utilize the system of this invention as a tubular or hollow fibre. In this embodiment, the polysulfone porous support layer may be extruded as a fine tube with a wall thickness of typically 0.001-0.1 mm. The extruded tubes are passed through a bath of polyvinyl alcohol which is crosslinked and cured in situ. A bundle of these tubes is secured (with an epoxy adhesive) at each end in a header; and the fibres are cut so that they are flush with the ends of the header. This tube bundle is mounted within a shell in a typical shell-and-tube assembly.

In operation, the charge liquid is admitted to the tube side and passes through the inside of the tubes and exits as retentate. During passage through the tubes, permeate passes through the non-porous separating layer and permeate is collected in the shell side.

In this embodiment, it will be apparent that the system may not normally include a carrier layer. In still another embodiment, the porous support layer may be omitted; and the separating layer is extruded and thereafter cross-linked and cured in situ prior to mounting in the headers.

PERVAPORATION

It is a feature of the non-porous polyvinyl alcohol separating layer that it is found to be particularly effective when used in a pervaporation process. In pervaporation, a charge liquid containing a more permeable and a less permeable component is maintained in contact with a non-porous separating layer; and a pressure drop is maintained across that layer. The charge liquid dissolves into the membrane and diffuses therethrough. The permeate which passes through the membrane and exits as a vapor may be recovered by condensing at low temperature or alternatively may be swept away by use of a moving stream of gas. Preferably, the permeate side of the membrane is maintained at a low pressure, typically 5 mm. Hg.

For general background on pervaporation, note U.S. Pat. Nos. 4,277,344; 4,039,440; 3,926,798; 3,950,247; 4,035,291; etc.

It is a feature of this invention that the novel membrane may be particularly useful in pervaporation processes for dewatering aqueous solutions of glycols containing at least two hydroxy groups on a carbon backbone, typified by glycols se such as ethylene glycol, propylene glycol, butylene glycols, etc. triols including glycerine, etc; glycol ethers including diethylene glycol, triethylene glycol, etc.

A typical charge may be a 50–99 w % say 85 w % aqueous solution of ethylene glycol.

In practice of the pervaporation process of this invention, the charge aqueous glycol solution at 40° C.–120° C., say 80° C. may be passed into contact with the non-porous separating layer of the membrane of this invention. A pressure drop of about one atmosphere is commonly maintained across the membrane. Typically, the feed or charge side of the membrane is at about atmospheric pressure and the permeate or discharge side of the membrane is at a pressure of about 2–50 preferably 5–20, say 10 mm.Hg.

The permeate which passes through the membrane includes water and a small proportion of the glycol from the charge liquid. Typically, the permeate contains 90–99.9, say 99 w % water. Permeate is recovered in vapor phase.

Pervaporation may typically be carried out at a flux of 0.1–10, say 0.50 gallons per square foot per day which corresponds to about 0.17–16.9, say 0.68 kilograms per square meter per hour (kmh). Typically, the units may have a selectivity (measured in terms of w % ethylene glycol in the permeate during pervaporation at 80° C. of an 85% aqueous solution of ethylene glycol through a standard polyvinyl alcohol separating layer of 2mm. thickness) of 0.3–1.0, say 0.5 w % ethylene glycol.

Practice of the process of this invention will be apparent to those skilled in the art from inspection of the following examples wherein, as elsewhere in this specification, all parts are parts by weight unless otherwise stated.

DESCRIPTION OF SPECIFIC EMBODIMENTS

EXAMPLE I

In this example, which represents the best mode presently known of carrying out the process of this invention, the selective separating layer was mounted on the porous support layer of a commercially available (from Film Tec Corp) composite containing a non-woven polyester backing as carrier layer bearing, as a porous support layer, a microporous polysulfone layer of molecular weight cut-off of 20,000. The selective separating layer was formed in situ by a one-step coating process. The separating layer was formed from a solution containing 10 g of 7 w % polyvinyl alcohol (M.W. of 115,000) in water to which was added 1.37 g of a 25 w % aqueous solution of glutaraldehyde and 0.15 g of 0.5 n sulfuric acid solution. This mixture was stirred until homogeneous and spread onto the polysulfone microporous support to form a film 4 mils thick. The assembly was cured in an oven for 15 minutes at 150° C.

The membrane was evaluated in pervaporation cells to which the charge at 80° C. was an aqueous solution containing 85 w % ethylene glycol and 15 w % water. Permeate pressure was 5 mm.Hg. The permeate condenser contained 0.4 w % ethylene glycol at a flux of 0.68 kilograms per square meter per hour (kmh). A typical prior art membrane as disclosed in European patent No. 0 096 339 A2 had a permeate containing 4.7 w % ethylene glycol at a flux of 0.22 kmh.

TABLE

|  | EG Content in permeate | Flux kmh |
| --- | --- | --- |
| Example I | 0.4 | 0.68 |
| Prior Art | 4.7 | 0.22 |

From the above table, it is apparent that the instant invention makes it possible to attain permeate desirably containing as little as 0.4 w % of ethylene glycol—which is only (0.4/4.7) 8.5% of that attained by the prior art. It is also apparent that the flux attained in Example I is desirably more than three times that attained by the control prior art.

EXAMPLES II–VII

In this series of examples, a composite membrane including a crosslinked polyvinyl alcohol was prepared and tested as in Example I—except that the curing temperature and time were varied. The results were as follows:

TABLE

| Example | Curing Conditions | | Membrane Performance | |
| --- | --- | --- | --- | --- |
|  | Temp (°C.) | Time (min) | Selectivity | Flux (kmh) |
| I | 150 | 15 | 0.4 | 0.68 |
| II | 125 | 15 | 0.5 | 0.75 |
| III | 100 | 15 | 2.5 | 0.75 |
| IV | 150 | 5 | 0.7 | 0.59 |
| V | 190 | 3 | 0.3 | 0.85 |
| VI | 225 | 3 | 0.1 | 0.17 |

From the above table, it is apparent that when the separating layer of polyvinyl alcohol is cured for shorter times, it is necessary to use higher temperatures in order to achieve a more selective membrane.

The longer a membrane system is cured at a given temperature (compare Examples I and IV), the desirably lower is the Selectivity.

EXAMPLES VIII–XI

In this series of examples, a crosslinked polyvinyl alcohol membrane system was prepared and tested as in Example I except that the amount of glutaraldehyde (i.e. the mole ratio of gluteraldehyde to polyvinyl alcohol) was varied.

TABLE

| Example | GA/PVA mole ratio | Membrane Performance | |
|---|---|---|---|
| | | Selectivity % EG | Flux kmh |
| VIII | 0.02 | 20 | 0.85 |
| IX | 0.08 | 10 | 1.19 |
| X | 0.12 | 4 | 1.10 |
| XI | 0.16 | 0.8 | 0.93 |

From the above table, it is apparent that high concentration of crosslinking agent is needed in order to obtain highly selective membranes. At a mole ratio of 0.02 (Example VIII) the Selectivity is 20%; and as the mole ratio increases to 0.16 (Example XI) the selectivity desirably decreases, to 0.8. Commonly, it is desired to utilize a mole ratio of 0.1–0.2 say about 0.15 as this provides a good balance between selectivity and flux.

EXAMPLE XII

In this example, the support layer and the carrier layer were as in Example I. The selective separating layer was formed in situ by a two-step coating process A first aqueous coating solution (10 g) contained 7 w % polyvinyl alcohol to which was added 1.37 g of 25 w % aqueous solution of glutaraldehyde. This mixture was stirred until homogeneous and spread on the polysulfone support with a knife blade to give a 4 mil. thick film which was oven dried at 50° C. for 4 minutes.

There was then spread on this dried film a 4 mil. film of second solution containing 10 g of 3.5 w % aqueous polyvinyl alcohol to which was added 0.15 g of 0.5N sulfuric acid which was mixed to homogeneity. The film was then oven cured for 15 minutes at 125° C.

Evaluation of the membrane system as in Example I gave a Selectivity of 0.28% and a flux of 0.48.

EXAMPLES XIII–XVIII

In this series of examples, the procedure of Example XII was followed except that in each of Examples XIII–XVII a different aldehyde (in place of the same amount of glutaraldehyde) was employed In Example XVIII, the procedure of Example XII was followed except that in place of sulfuric acid, an equal number of grams of 0.5N aqueous hydrochloric acid was used. The results are as follows:

TABLE

| Example | Crosslinking Agent | Acid Catalyst | Membrane Performance | |
|---|---|---|---|---|
| | | | Selectivity % EG | Flux kmh |
| XII | glutaraldehyde | sulfuric | 0.28 | 0.48 |
| XIII | 2-hydroxyhexane-dial | sulfuric | 0.18 | 0.30 |
| XIV | glyoxal | sulfuric | 2.61 | 0.16 |
| XV | formaldehyde | sulfuric | 4.01 | 0.71 |
| XVI | succinic acid | sulfuric | 3.04 | 0.76 |
| XVII | succinic acid semialdehyde | sulfuric | 8.71 | 0.75 |
| XVIII | glutaraldehyde | hydrochloric | 1.75 | 0.87 |

From the above table, it is apparent that putative crosslinking agents containing only one aldehyde group (Examples XV or XVII) or no aldehyde groups (Example XVI) are characterized by an undesirably low selectivity. Agents containing only two carbon atoms (glyoxal of Example XIV) are characterized by undesirably low selectivity. Example XVIII shows that use of hydrochloric acid as acid catalyst is much less satisfactory (than for Example XII) in that, it undesirably gives a much higher selectivity although the flux is significantly higher.

Although this invention has been illustrated by reference to specific embodiments, it will be apparent to those skilled in the art that various changes and modifications may be made which clearly fall within the scope of this invention.

We claim:

1. A non-porous separating layer of thickness of 1–10 microns of cast polyvinyl alcohol of molecular weight $\overline{M}_n$ of 20,000–200,000 which has been cross-linked, in the presence of acid catalyst, with an aliphatic polyaldehyde containing at least three carbon atoms including those in said aldehyde groups, the mole ratio of aldehyde to vinyl alcohol being 0.05–0.30, and thereafter cured at 100°–200° C.

2. A non-porous separating layer of thickness of 1–5 microns of cast polyvinyl alcohol of molecular weight $\overline{M}_n$ 20,000–200,000 which has been cross-linked in the presence of acid catalyst, with glutaraldehyde, the mole ratio of aldehyde to vinyl alcohol being 0.05–0.30, and thereafter cured at 100° C.–200° C.

3. A non-porous separating layer of thickness of 1–10 microns of cast polyvinyl alcohol of molecular weight $\overline{M}_n$ of 20,000–200,000 which has been cross-linked in the presence of acid catalyst, with an aliphatic polyaldehyde containing at least three carbon atoms including those in said aldehyde groups, the mole ratio of aldehyde to vinyl alcohol being 0.05–0.30, and thereafter cured at 100° C.–200° C.; and a porous support layer, onto which said separating layer is cast, of a polysulfone of molecular weight cutoff less than about 25,000.

4. A porous support layer of isopropylidene—free polysulfone of molecular weight $\overline{M}_n$ of 25,000–100,000, a thickness of about 40–80 microns, and a molecular weight cutoff of about 20,000 having cast thereon a non-porous separating layer of thickness of 1–10 microns of cast polyvinyl alcohol of molecular weight $\overline{M}_n$ of 20,000–200,000 which has been cross-linked, in the presence of acid catalyst, with glutaraldehyde, the ratio of aldehyde to vinyl alcohol being 0.05–0.30, and thereafter cured at 100° C.–200° C.

5. A porous support layer of isopropylidene-free polysylfone of molecular weight $\overline{M}_n$ 25,000–100,000, a thickness of about 40–80 microns, and a molecular weight cutoff of about 20,000 having cast thereon a non-porous separating layer of thickness 1–10 microns of cast polyvinyl alcohol of molecular weight $\overline{M}_n$ of 20,000–200,000 which has been cross-linked, in the presence of acid catalyst, with glutaraldehyde, the mole ratio of aldehyde to vinyl alcohol being 0.05–0.30, and thereafter cured at 100° C.

* * * * *